United States Patent [19]

Goto et al.

[11] Patent Number: 4,555,510
[45] Date of Patent: Nov. 26, 1985

[54] THERAPEUTIC AGENT FOR HYPERTENSION

[75] Inventors: Kazuhiro Goto, Nakatsu; Osamu Yaoka, Fukuoka; Takanori Oe, Nakatsu, all of Japan

[73] Assignee: Yoshitomi Pharmaceutical Industries, Ltd., Osaka, Japan

[21] Appl. No.: 626,837

[22] PCT Filed: Oct. 30, 1982

[86] PCT No.: PCT/JP82/00425
§ 371 Date: Jun. 27, 1984
§ 102(e) Date: Jun. 27, 1984

[87] PCT Pub. No.: WO84/01711
PCT Pub. Date: May 10, 1984

[51] Int. Cl.$^4$ .......................................... A61K 31/435
[52] U.S. Cl. .................................................. 514/291
[58] Field of Search .......................................... 424/256

[56] References Cited

U.S. PATENT DOCUMENTS 4,085,111 4/1978 Oe et al. .......................... 260/296 H
4,281,001 7/1981 Maruyama et al. ................. 424/256

FOREIGN PATENT DOCUMENTS 58-39621 3/1983 Japan .................................. 424/256

OTHER PUBLICATIONS

Derwent CPI 73235, E/35.
Derwent CPI 87793, X/47.

*Primary Examiner*—Albert T. Meyers
*Assistant Examiner*—Joyce L. Morrison
*Attorney, Agent, or Firm*—Wenderoth, Lind & Ponack

[57] ABSTRACT

An agent for the therapy of hypertension, which comprises as an effective component at least one compound selected from the group consisting of 9-chloro-5-oxo-7-(1H-tetrazol-5-yl)-5H-[1]benzopyrano[2,3-b]pyridine, a salt thereof and hydrates thereof.

2 Claims, No Drawings

THERAPEUTIC AGENT FOR HYPERTENSION

This invention relates to a therapeutic agent for hypertension, which comprises, as an effective component, at least one compound selected from the group consisting of 9-chloro-5-oxo-7-(1H-tetrazol-5-yl)-5H-[1]benzopyrano[2,3-b]pyridine represented by the formula

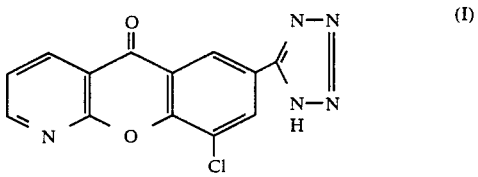

a salt thereof (e.g. sodium salt, potassium salt, calcium salt, ammonium salt or triethylamine salt) and hydrates thereof [hereinafter these compounds may sometimes be collectively called "Compounds (I)"].

The Assignee disclosed for the first time in the Japanese Patent Application laid open (Kokai) No. 151897/1975 (Japanese Patent Publication No. 16432/1980) that the compounds (I) are useful as antiallergic agents, etc. Sodium salt.pentahydrate of the compound of formula (I) has, as disclosed in, for example, "Shinyaku to Rinsho" (Journal of New Remedies & Clinics) Vol. 29, pp. 1991 (1980), been clinically used as ana antiallergic agent or an agent for bronchial asthma.

The inventors have studied further for a novel use of the compounds (I), and have found that the compounds (I) significantly lower blood pressure, thus having established the present invention.

In general, long-lasting hypertension increases the stress upon the heart, is apt to invite cardiac insufficiency, accelerates arteriosclerosis, and enhances the risk of causing cerebral hemorrhage, cardiac infarction or renal insufficiency. Further, it is said that the frequency of occurrence of secondary disorders is influenced by the level of blood pressure. However, abrupt lowering of blood pressure in hypertension patients is said to cause orthostatic hypotensive asthenia. Therefore, it has been desired to develop an agent which shows mild blood pressure-lowering actions with less side effects.

The compounds (I) of this invention, as shown clearly by the following experiments, act mildly in the therapy or prophylaxis of hypertension to apparently lower blood pressure depending on given dosages. The toxicity of the compounds (I) is remarkably low. For example, $LD_{50}$ in mice and rats is 16,000 mg/kg or more by oral administration. Besides, when the compounds (I) are clinically used as an antiallergic agent, 'practically no side-effects are observed. From the foregoing, the compounds (I) can be considered as an ideal agent for the therapy of hypertension.

By the following experimental examples, the present invention will be explained concretely.

TEST COMPOUND

Compound A:
9-chloro-5-oxo-7-(1H-tetrazol-5-yl)-5H-[1]benzopyrano[2,3-b]pyridine·sodium salt·pentahydrate

Test Method

1. Blood Pressure Measurement

Rats were fixed without anesthesia and warmed at 40° C. in a thermostat for 10 minutes. The blood pressure was measured at room temperature by an indirect manometer (manufactured by NARCO Co., PE-300).

The pulse of the rat tail artery was detected with a pulse transducer and recorded on a recorder (manufactured by Hitachi, Ltd., 056 Type), and the maximal blood pressure was read.

2. Action on rats having renal hypertension

Rats having renal hypertension induced in the manner described by I. H. Page [Science 89, 273 (1939)] were used as the test animals. The test compound was orally administered once a day for 28 successive days. The blood pressure was measured five hours after the administration at intervals of one week.

3. Action in the course of causing hypertension in SHR

Young male SHRs weighing about 70 g at 5 week-old were employed. They were orally given the test compound once daily for 28 successive days. The blood pressure was measured five hours after the administration at intervals of one week.

Test Results

1. The compound A showed, as seen in the following Table 1, hypotensive action in rats having renal hypertension depending on the dosages.

2. The compound A inhibited the ascending of blood pressure due to aging, as shown by the following Table 2, depending on the dosages, in the course of causing hypertension in SHR, on and after the 14th day after the administration.

TABLE 1

(Action on Rats having Renal Hypertension)

| Compound | Dosage p.o. (mg/kg) | Number of Rats° | Blood Pressure (mmHg) | | | | | |
|---|---|---|---|---|---|---|---|---|
| | | | Before Administration | After Administration (day) | | | | |
| | | | | 1 | 7 | 14 | 21 | 28 |
| Control (0.5% M.C.) | — | 8 | 199 ± 8 | 194 ± 8 | 189 ± 11 | 183 ± 9 | 188 ± 13 | 194 ± 11 |
| Compound A | 30 | 9 | 194 ± 8 | 178 ± 7 | 163 ± 5* | 170 ± 9 | 166 ± 9 | 162 ± 4** |
| | 300 | 10 | 188 ± 6 | 173 ± 8* | 162 ± 10* | 153 ± 6** | 157 ± 6* | 160 ± 6** |

*$P < 0.05$,
**$P < 0.01$

TABLE 2

| | | Number | Blood Pressure (mmHg) | | | | | |
|---|---|---|---|---|---|---|---|---|
| | | | (Action upon the Course of Ascending Hypertension on SHR) | | | | | |
| | Dosage | of | Before | After Administration (day) | | | | |
| Compound | p.o. (mg/kg) | Rats | Administration | 1 | 7 | 14 | 21 | 28 |
| Control (0.5% M.C.) | — | 8 | 111 ± 3 | 112 ± 3 | 133 ± 3 | 158 ± 2 | 162 ± 2 | 166 ± 3 |
| Compound A | 30 | 9 | 126 ± 3 | 130 ± 4 | 133 ± 4 | 143 ± 3** | 144 ± 3** | 150 ± 3** |
| | 300 | 6 | 126 ± 5 | 129 ± 2 | 131 ± 4 | 133 ± 4** | 134 ± 2** | 142 ± 4** |

**$P < 0.01$

Thus, the compounds (I) can be safely used in a form of common pharmaceutical preparations with suitable and common carriers, for the therapy and prophylaxis of hypertension without causing any undesirable side effects.

The pharmaceutical preparations can take common forms such as capsules, tablets, powder or fine granules for oral administration. For example, tablets each containing 60 mg of the compound of this invention or 10% fine granules can be prepared with the following composition.

60 mg tablets
Compound (A) (as anhydride): 60.0 mg
Calcium carboxymethyl cellulose: 130.2
Hydroxypropyl cellulose: 3.5
Magnesium metasilicate aluminate: 28.5
Talc: 3.0
Magnesium stearate: 2.25
10% fine granules
Compound (A) (as anhydride): 500 g
Sodium bicarbonate: 250
D-mannit: 4060
Hydroxypropyl cellulose: 45
Talc: 5

The dosage of compound (A) somewhat varies according to the subject diseases, symptoms, etc, but, it is in the range of 120 to 720 mg per day for adult humans, in case of oral administration.

We claim:

1. A method of treating a human afflicted with hypertension, which comprises orally administering to the human a therapeutically effective amount of a compound selected from the group consisting of 9-chloro-5-oxo-7-(1H-tetrazol-5-yl)-5H-[1]benzopyrano[2,3-b]pyridine, a pharmaceutically effective salt thereof and the sodium salt.penta hydrate thereof.

2. A method as claimed in claim 1, wherein the compound administered is 9-chloro-5-oxo-7-(1H-tetrazol-5-yl)-5H-[1]benzopyrano[2,3-b]pyridine·sodium salt·pentahydrate.

* * * * *